United States Patent [19]

Paasen et al.

[11] 3,946,076

[45] Mar. 23, 1976

[54] CONTINUOUS PROCESS FOR RECOVERY OF CYCLOHEXANONE

[75] Inventors: Mathijs M. F. Paasen, Oirsbeek; Harrie H. J. Meijerink, Geleen, both of Netherlands

[73] Assignee: Stamicarbon, N.V., Geleen, Netherlands

[22] Filed: Oct. 13, 1972

[21] Appl. No.: 297,448

[30]    Foreign Application Priority Data

Oct. 14, 1971   Netherlands..................... 7114111

[52] U.S. Cl............................ 260/586 P; 260/631 R
[51] Int. Cl.²......... C07C 27/12; C07C 29/00; C07C 45/02
[58] Field of Search ..................... 260/586 B, 631 R

[56]            References Cited
               UNITED STATES PATENTS

| | | | |
|---|---|---|---|
| 2,931,834 | 4/1960 | Crouch et al. .................. | 260/586 B |
| 3,275,692 | 9/1966 | Pochler et al. .................. | 260/586 B |
| 3,316,302 | 4/1967 | Steeman et al. ................. | 260/586 B |
| 3,439,041 | 4/1969 | Gey et al. ......................... | 260/586 B |

*Primary Examiner*—Norman Morgenstern
*Attorney, Agent, or Firm*—Cushman, Darby & Cushman

[57]            ABSTRACT

Cyclohexanone is recovered in the processing of the reaction product of the oxidation of cyclohexane to cyclohexanone by removing water from the reaction product prior to the initial distillation and separation step. Quantities of cyclohexanone that were previously discarded are now removed in a convenient and economical manner.

2 Claims, 2 Drawing Figures

CONTINUOUS PROCESS FOR RECOVERY OF CYCLOHEXANONE

This invention relates to a continuous process for recovery of high-purity cyclohexanone.

Cyclohexanone, a starting material for caprolactam, is now made in large quantities by oxidation of cyclohexane.

The oxidation of cyclohexane is usually carried out in the liquid phase at temperatures of 75°–200°C, generally 120°–160°C, at atmospheric or at elevated pressure, e.g. 1–50 atm, usually 5–15 atm. Catalysts normally employed for this purpose are cobalt or manganese compounds, e.g. cobalt naphthenate or cobalt octoate.

This process yields cyclohexanol and cyclohexanone as the principal oxidation products, as well as acids like adipic acid, glutaric acid, valeric acid, hydroxycapropic acid, succinic acid, formic acid, acetic acid, and esters of these acids with cyclohexanol. Since the yield of cyclohexanol and cyclohexanone decreases with increasing conversion of cyclohexane, the reaction is conducted to a conversion factor normally at a value between 3 and 15%. As a result, the liquid crude oxidation product leaving the oxidation reactor contains a large excess of cyclohexane, in addition to cyclohexanol, cyclohexanone, acids, esters and water as mentioned.

It is customary, in processing the crude oxidation product, first to remove the acids by neutralization, in order to prevent corrosion taking place in the processing installation. In addition, part of the amount of the ester is saponified during this treatment. Next, nonconverted cyclohexane is recovered by distillation, and fed back to the oxidation reactors. After that, ester left in the remaining product is saponified to raise the yield of cyclohexanol. From the organic phase obtained from the saponification stage — mainly cyclohexanol and cyclohexanone, plus minor quantities of impurities — a light fraction containing impurities is removed by preliminary distillation, whereupon the bottom product from the preliminary distillation stage is redistilled and the desired product — cyclohexanone — is recovered as the top product.

From the bottom product of the cyclohexanone distillation a fraction consisting mainly of cyclohexanol is separated off, and subsequently subjected to a dehydrogenation treatment. The resulting conversion product — cyclohexanone, a large quantity of cyclohexanol plus minor quantities of by products — is fed back to the preliminary distillation and passed through the entire distillation process.

Recovery of cyclohexanone by distillation, starting from neutralized oxidation product freed of nonconverted cyclohexane, combined with dehydrogenation of the cyclohexanol fraction to cyclohexanone and recirculation of the conversion product to the preliminary distillation stage, is already known from British patent specification 913,000 (the entire disclosure of which is hereby incorporated by reference) and notably from example 2 contained therein.

It has appeared, however, that in the application of this known processing technique, the top product from the preliminary distillation contains not only the light components, but also some cyclohexanone and cyclohexanol and recovery of the latter two would call for a laborious, uneconomical after-distillation of the top product and for this reason the after distillation step is omitted in practice, with the result that valuable cyclohexanone and cyclohexanol are lost.

DETAILED DESCRIPTION OF THE INVENTION

The present invention provides a process for reducing the loss of cyclohexanone and cyclohexanol in economically significant amounts from top products of the preliminary distillation that in the past have been discarded.

Investigation has shown that the presence of cyclohexanone and cyclohexanol in the top product of the preliminary distillation is due to the fact that with the dehydrogenation of cyclohexanol there invariably occurs the formation of a small amount of water as one of the byproducts which in the preliminary distillation is distilled in a fixed ratio to cyclohexanone and cyclohexanol along with the light components.

The amount of water formed in the dehydrogenation of cyclohexanol is of the order of about 0.25–0.5% wt. calculated on the amount of dehydrogenation product. The amount of cyclohexanone and cyclohexanol distilled along with the water in the top product is approximately 6 times the amount of water, that is approximately 1.5–3% wt. relative to the amount of dehydrogenation product.

The object of the present invention is to minimize the amount of cyclohexanone and cyclohexanol lost through formation of water in the dehydrogenation of cyclohexanol. The recovery of from 1.5 to 3% wt. of cyclohexanone and cyclohexanol, when considered in a high volume process, is indeed a substantial cost savings.

The present invention relates to a continuous process for recovering cyclohexanone by distillation from the conversion product obtained in the dehydrogenation of cyclohexanol and containing cyclohexanone, cyclohexanol and small amounts of impurities, including water, and is characterized in that the conversion product is first subjected to a treatment for removal of water, and, next, is separated by distillation where the components having a lower boiling point than cyclohexanone are distilled off and, subsequently, cyclohexanone is separated from the higher-boiling components. The removal of water can be carried out by directing the conversion product over a dehydrating agent, such as concentrated sulphuric acid, calcium oxide, silica gel or the like, in a drying column, or by means of molecular sieves. A specially suited method for removing the water is azeotropic distillation by means of cyclohexane. All or substantially all of the water is removed from the conversion product.

A preferred mode of practicing the present process is to subject the conversion product from the dehydrogenation of the cyclohexanol fraction, together with the oxidation product freed of acids, esters and nonconverted cyclohexane, to a treatment for removal of water, consisting of azeotropic distillation with the aid of cyclohexane. In the azeotropic distillation step temperatures of the order of about 50°–100°C are used, preferably 75°–85°C. The pressure may be atmospheric or higher, for instance in the range of 1–3 atmospheres. The process of azeotropic distillation of such materials is known, for example from CIOS-report XXXIII-50, part II page 608, FIG. 115, according to which, first a cyclohexane-water mixture is distilled off from its admixture with cyclohexanol and cyclohexanon, the disclosure of which is hereby incorporated by reference. As indicated, although the process itself is generally known, it has, prior to the present process, not been employed in such a reaction scheme.

In some instances it is desirable to add cyclohexane to aid in separation and this addition of cyclohexane to the mixture to be treated may be done in the drying column. If, after saponification of the esters, cyclohexane is supplied to the cyclohexane oxidation product to achieve a good separation between the organic and aqueous phases, as is suggested in U.S. Pat. No. 3,316,302, the disclosure of which is hereby incorporated by reference, the mixture to be dried will contain sufficient cyclohexane to enable the water to be removed as cyclohexane-water azeotrope, and the addition of cyclohexane can be omitted.

The process according to the invention will now be further elucidated with reference to the FIGS. 1 and 2 and the Example.

Figure 1:
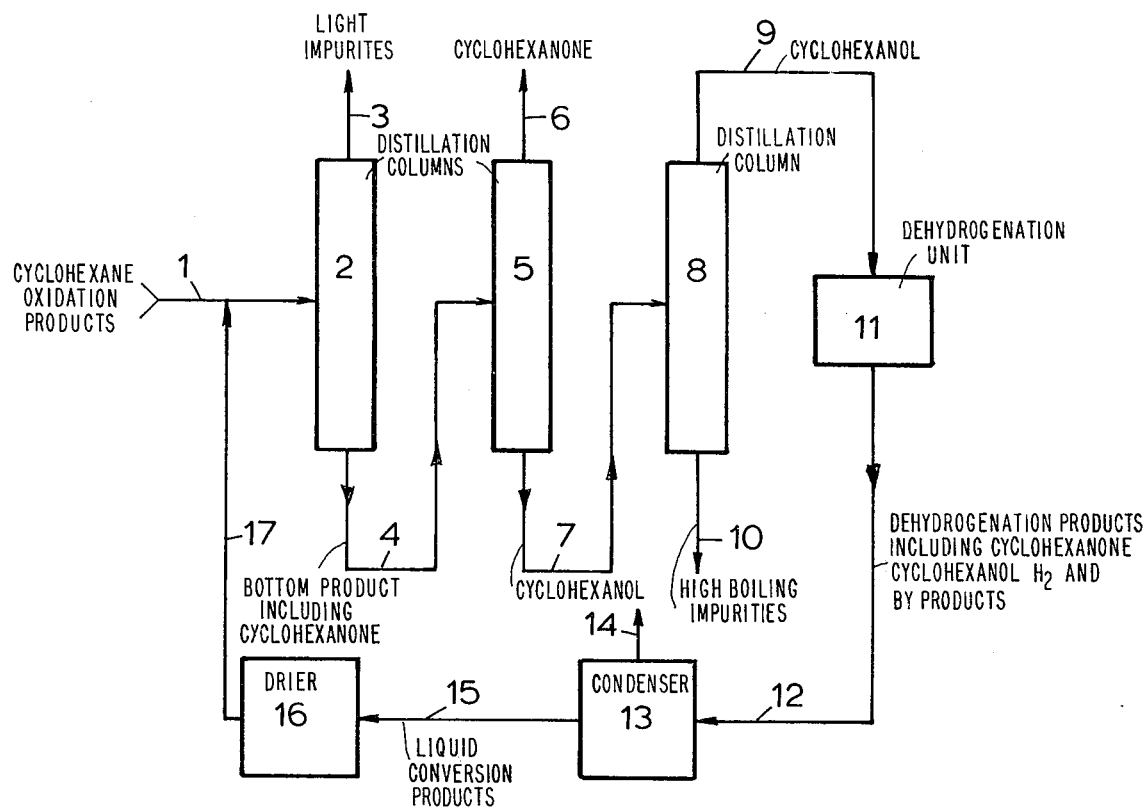
FIG. 1 is a schematic representation of the process.

In FIG. 1 the oxidation product of cyclohexane, from which acids, esters and nonconverted cyclohexane have been removed, is fed to a preliminary distillation column 2 along a line 1. In column 2 the light impurities are removed as top product along line 3. From the bottom product of column 2, which is fed to column 5 along line 4, pure cyclohexanone is recovered by distillation along line 6. The remaining product leaves column 5 along line 7 and flows to column 8, where cyclohexanol is distilled off as top product, which is then fed along line 9 to dehydrogenation unit 11 to be converted there into a cyclohexanone-containing product by means of a suited cayalyst. The bottom product from column 8, which consists of high-boiling impurities, is removed from the system along line 10. The conversion product obtained in dehydrogenation unit 11, consisting of cyclohexanone, cyclohexanol, hydrogen and byproducts, passes through line 12 to condenser 13, from which the hydrogen formed in the dehydrogenation is discharged along line 14. Line 15 feeds the liquid conversion product to a drier 16, from which the dried product flows along line 17 into line 1.

Figure 2:
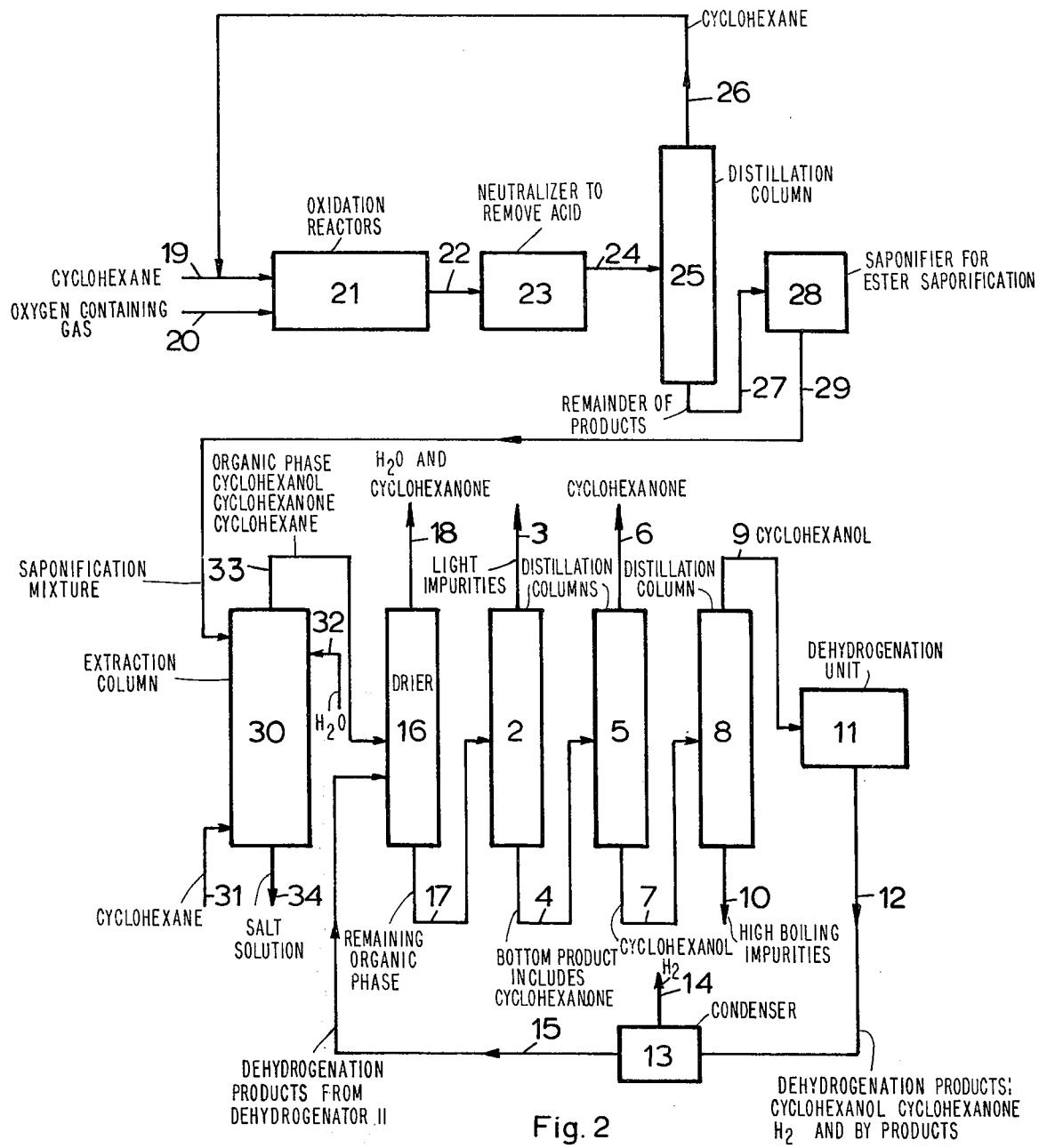
FIG. 2 is a schematic representation of a preferred process wherein water is removed by azeotropic distillation.

FIG. 2 shows schematically the process in which the conversion product obtained in the hydrogenation step together with the cyclohexane oxidation product freed of acids, esters and nonconverted cyclohexane, is subjected to a treatment for removal of water by means of azeotropic distillation with the aid of cyclohexane supplied to the oxidation product after saponification of the esters. Reference numbers 2 up to and including 17 denote the same units as the corresponding numbers in FIG. 1; the reference numbers 19 up to and including 33 relate to the equipment for oxidizing the cyclohexane and processing the crude oxidation product to a cyclohexanol-cyclohexanone mixture.

Reference 21 in FIG. 2 denotes a battery of reactors in which cyclohexane, supplied along line 19 is oxidized in the liquid phase with an oxygen containing gas supplied along line 20. The crude oxidation product flows along line 22 to a neutralizer 23, while the acid-free organic phase passes through line 24 to a distillation column 25 where nonconverted cyclohexane is separated off, to be next recycled along line 26. The remaining product passes along line 27 to a saponifying reactor 28, where the esters are saponified. The mixture formed in the saponification flows along line 29 into extraction column 30 which additionally receives an amount of cyclohexane from line 31 to effect a good separation between the organic phase and the salt solution formed, as well as an amount of water from line 32 for washing any salts left out of the organic phase. The salt solution is drained along line 34. Line 33 feeds the organic phase, consisting substantially of cyclohexanol, cyclohexanone, cyclohexane with minor quantities of impurities, to drying column 16 into which also the cyclohexanone-containing dehydrogenation product from dehydrogenation reactor 11 is introduced via line 12, condenser 13 and line 15. The hydrogen formed in dehydrogenation reactor 11 is removed from the system via condenser 13 and line 14. The water present in the mixture and the cyclohexane are withdrawn from drying column 16 along line 18 and separated in a separator (not shown). The resulting cyclohexane is recycled, e.g. by feeding it into line 26 or line 31. The remaining organic phase is supplied to distillation column 2, via line 17, for removing components having a boiling point lower than the organic phase, whereupon the mixture is further processed in the manner described pertaining to FIG. 1.

In practicing the process as shown schematically in FIG. 2, the removal of the cyclohexane-water azeotrope is carried out in the existing drying column 16. Of course, the capacity of the distillation column will have to be enlarged, but, on the other hand, there is the possibility that the preliminary distillation may be reduced in capacity.

EXAMPLE

In a long-duration experiment 260 kgs/h of cyclohexanone and cyclohexanol were fed to drying column 16 for producing 100 kgs/h of cyclohexanone in accordance with the process of FIG. 2. 140 kgs of this quantity came from the dehydrogenation of cyclohexanol via line 15. The water content of the conversion product supplied along line 15 varied during the experiment from 0.35 to 0.49 % wt. Drying column 16 was operated at atmospheric pressure and at 80°C, and preliminary distillation column 2 at 400 mm Hg absolute pressure at 115°C. In columns 5 and 8 an absolute pressure of 45 mm Hg was maintained with temperatures of 73° and 87°C, respectively. The water content of the bottom product from drying column 16 had decreased to 0.02–0.98% wt. The top product from preliminary distillation column 2 contained an amount of cyclohexanone which, depending on the water content, varied from 0.12 to 0.48 kg per hour.

If, in contrast to the present invention, but with all other conditions remaining unchanged, the conversion product was directly fed to preliminary distillation column 2 and drying column 16 was not used, the water content in column 2 varied from 0.36 to 0.53% wt. The amount of cyclohexanone distilled as top product along with the light fraction, was 2.16–3.18 kgs/h, depending on the water content. This shows that in practice the present process substantially reduces the loss of cyclohexanone by approximately 2–2.7% calculated to the amount of cyclohexanone end product.

What is claimed is:

1. In a process for the oxidation of cyclohexane to cyclohexanone comprising:
   a. reacting cyclohexane and oxygen at a temperature of 75°–200°C and a pressure of 1–50 atmospheres to produce a reaction product comprising cyclohexanol and cyclohexanone;
   b. removing acids from the reaction product;

c. recovering nonconverted cyclohexane from the reaction product by distillation and returning it to the oxidization zone of step (a);
d. saponifying the remaining reaction product to increase the yield of cyclohexanol;
e. thereafter first distilling off and discarding a light or top fraction from the reaction product, which light fraction contains substantially all products with boil-point under the prevalent distillation conditions below that of cyclohexanone;
f. further distilling the reaction product to recover cyclohexanone as a second light fraction and to produce a bottom product containing cyclohexanol;
g. dehydrogenating cyclohexanol from the bottom product of step (f) to produce a conversion product containing cyclohexanone and cyclohexanol and introducing this conversion product back into the process at step (e);

the improvement comprising:

removing substantially all of the water from the conversion product of step (g) by azeotropic distillation in the presence of cyclohexane as a separating agent, before directing this conversion product to distillation step (e).

2. The process of claim 1, wherein said azeotropic distillation is conducted at temperatures between 50° and 100°C.